United States Patent [19]

Maltz

[11] 4,409,138

[45] Oct. 11, 1983

[54] NON-ABSORBABLE COMPOUNDS OF MUCOLYTIC ACTIVITY, THE PROCESS FOR THEIR PREPARATION, AND THERAPEUTIC COMPOSITIONS WHICH CONTAIN THEM AS ACTIVE PRINCIPLE

[75] Inventor: Javier E. Maltz, Buenos Aires, Argentina

[73] Assignee: Etablissement Texcontor, Vaduz, Liechtenstein

[21] Appl. No.: 184,249

[22] Filed: Sep. 5, 1980

[30] Foreign Application Priority Data

Jul. 1, 1980 [IT] Italy ............................... 23161 A/80

[51] Int. Cl.³ ..................... C07G 7/00; C08B 37/00; A61K 37/02
[52] U.S. Cl. ............................ 260/112 R; 536/4.1; 424/177; 424/180
[58] Field of Search .................... 424/177, 180, 94; 260/112 R, 112.5 R; 536/4.1, 18

[56] References Cited

U.S. PATENT DOCUMENTS

| | | | |
|---|---|---|---|
| 3,639,213 | 2/1972 | Ginger et al. | 424/94 |
| 3,683,069 | 8/1972 | Hooreman | 424/94 |
| 4,004,979 | 1/1977 | Avrameas et al. | 260/112 R |
| 4,185,090 | 1/1980 | McIntire | 424/94 |
| 4,259,233 | 3/1981 | Carrico et al. | 536/4 |

FOREIGN PATENT DOCUMENTS 1390542 4/1975 United Kingdom .

OTHER PUBLICATIONS

Russian Chemical Reviews, vol. 45, No. 11, 1976; pp. 1067–1075; Author: W. Marconi.

*Primary Examiner*—Blondel Hazel
*Attorney, Agent, or Firm*—Stevens, Davis, Miller & Mosher

[57] ABSTRACT

Marcromolecular compounds of mucolytic activity, non-absorbable by tissues, free from side-effects, compatible with antibiotics, and constituted by carbohydrates as their basic structure, to which enzymes and sulphydryl groups are bonded by suitable aliphatic chains.

2 Claims, No Drawings

NON-ABSORBABLE COMPOUNDS OF MUCOLYTIC ACTIVITY, THE PROCESS FOR THEIR PREPARATION, AND THERAPEUTIC COMPOSITIONS WHICH CONTAIN THEM AS ACTIVE PRINCIPLE

The present invention relates to new compounds of topical mucolytic activity in particular on secretions of the respiratory passages, which are not absorbed by the tissues with which they come into contact, but are able to reach the gastrointestinal tract unaltered, where they are metabolized to non-toxic products which can be completely eliminated.

The present invention also relates to the process for preparing the new mucolytic agents, and therapeutic compositions of mucolytic activity, in particular in affections of the respiratory passages, comprising the new compound according to the present invention as their active principle.

More precisely, the present invention relates to new macromolecular mucolytic agents having a molecular weight of between 10,000 and 300,000, constituted by carbohydrates as their basic structure, to which -SH sulphydryl groups and enzymes are bonded by suitable aliphatic chains.

In the medical field, the problem of affections of the respiratory passages with consequent secretion of mucus is always a considerable problem, for which a completely effective drug has not yet been discovered (the American Journal of Medicine Vol. 49, July 1970, pages 1-4 "The appropriate use of mucolytic agents").

The problem is more serious and the mucus more difficult to eliminate when in the form of purulent mucus.

Of the known drugs possessing mucolytic activity both on purulent mucus and on non-purulent mucus, the most well known is N-acetylcysteine.

However, this substance has a certain number of considerable drawbacks. Namely, it has an unpleasant odor, it can cause bronchospasms, and when nebulized in fairly strong doses it has an irritating effect and causes coughing attacks. Furthermore, it has a deactivating effect on antibiotics, as a result of which it cannot be used in combination therewith.

More recently, good results have been obtained in attacking purulent mucus by using enzymes such as trypsin, chymotrypsin and deoxyribonuclease. Of these, trypsin and chymotrypsin act both on simple mucus and on purulent mucus, whereas deoxyribonuclease acts only on purulent mucus. However, the use of these enzymes has been discouraged due to the fact that they are absorbed by the tissues of the respiratory passages, thereby causing irritation of the pharynx and diffused proteolytic action on the blood and pulmonary tissues in subjects possessing low alpha-antitrypsin activity. As patients suffering from pulmonary illnesses frequently have a low alpha-antitrypsin activity, the use of enzymes as mucolytic agents has been practically abandoned, unless the subjects are under continuous medical control.

New mucolytic products both for non-purulent mucus and for purulent mucus have now been discovered and form the subject matter of the present invention, which are not absorbed by the mucus membranes of the respiratory tracts, and therefore do not give rise to proteolytic or allergic side-effects of either the inflammatory or hemolytic type. Moreover, the new products are compatible with antibiotics.

The new products of the present invention are represented by the general formula:

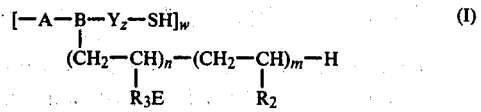

in which —A—B— represents a carbohydrate residue, with A equal to or different from B, Y is a radical able to bond the sulphydryl groups to the carbohydrate molecules, $R_3$ is a residue of $R_1$, $R_1$ is a functional group able to bond the enzyme to the synthesis macromolecules, E is an enzyme radical, $R_2$ is a functional group able to regulate the solubility of the product, n is 1 to 2000, m is 0 to 1000, w is 1 to 100, and z is 0 to 10, each carbohydrate unit being able to carry one or more enzyme residues, one or more sulphydryl groups or even different radicals, which are not essential for the purposes of the present invention.

The carbohydrate radical —A—B— is preferably the radical of a disaccharide such as saccharose or cellobiose, of an oligosaccharide containing 3 to 6 monosaccharide units, or of a polysaccharide of low molecular weight, generally not exceeding 10,000.

The enzyme radical E is the radical of an enzyme, preferably trypsin, chymotrypsin, deoxyribonuclease, streptokinase, neuroamidase, bromexin or papain.

$R_1$ and $R_2$, which are the same or different, are preferably:

—COOH, —COCl, —CONH$_2$, —COOCH$_3$,

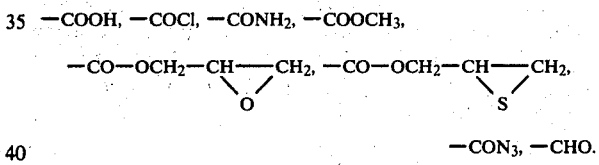

—CON$_3$, —CHO.

The solubility or dispersability of the new products can be adjusted by regulating the type and quantity of the $R_2$ groups present in the macromolecule. When z is other than zero, the aliphatic chains Y are preferably chosen from the group consisting of

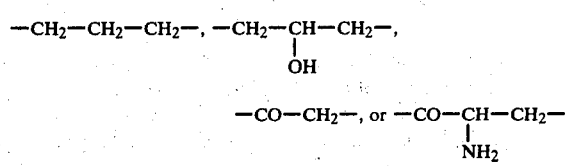

The enzyme radicals are preferably joined to the secondary hydroxyls, while the —SH groups are preferably bonded to the primary hydroxyls of the carbohydrate.

The new products of the present invention are prepared by following a multistage process comprising essentially a reaction in which a carbohydrate is copolymerized with vinyl monomers, a reaction with an enzyme, and a sulphdrylation reaction.

Essentially, the process according to the present invention consists of reacting a carbohydrate chosen from the group consisting of disaccharides, oligosaccharides of 3-6 units, and polysaccharides of molecular weight generally not exceeding 10,000, either simple or sulphydrylated, with one or more vinyl compounds of formula:

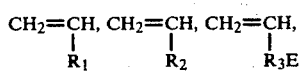

in which $R_1$, $R_2$, $R_3E$ are as heretofore defined.

If the vinyl monomers do not contain enzyme radicals, the obtained polymer of formula:

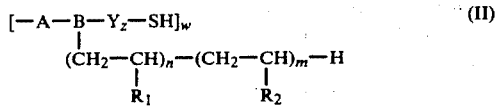

is reacted either directly or by way of suitable difunctional compounds with an enzyme if Z is other than 0, whereas if Z is 0 then it is sulphydrylated either before or after the reaction with an enzyme, this reaction being either direct or by way of suitable difunctional compounds.

Each of the stages indicated schematically heretofore can be carried out in various alternatives which are summarized hereinafter, with reference for clarity and simplicity to a disaccharide.

(1) The carbohydrate is reacted with one or more vinyl monomers in an aqueous or aqueous-organic medium by means of initiation mechanisms of radical type such as are obtained by using as the initiator a salt of $Ce^{4+}$ or $V^{5+}$ or a redox system of the $Fe^{++}/H_2O_2$, $Na_2S_2O_3/H_2O_2$, $Na_2S_2O_3/Na_2S_2O_8$, $R-SH/H_2O_2$ or similar type; or alternatively by transfer or decomposition reactions of functional peroxide groups, or diazonium salts present on derivatized carbohydrates; or again by the use of ionizing or UV radiation in the presence of photosensitisers.

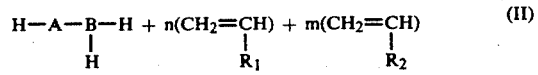

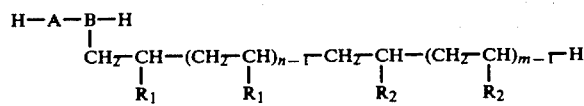

in which $R_1$ and $R_2$, which are the same or equal, are as heretofore defined. If a $Ce^{4+}$ salt is used as initiator, the synthetic polymer chain is bonded to the hydroxyl oxygen of the carbon in position 2 or 3 of the hexose and/or pentose component of the disaccharide (II). With other initiation systems, it is more difficult to establish the point of attack of the synthetic macromolecule.

The molecular weight of the synthetic component of the product obtained is between 10,000 and 300,000. Working in an aqueous medium favours formation of just a few polyvinyl chains of relatively high molecular weight. Working in an aqueous-organic medium favours the formation of a relatively large number of polyvinyl chains of relatively low molecular weight.

The organic solvents which can be used are preferably methanol, acetone, tetrahydrofuran, dimethylformamide, acetonitrile and the like.

To obtain compounds of relatively high molecular weight, it is necessary to operate in a mixture of solvents comprising 90 to 50 parts by weight of $H_2O$ and 10 to 50 parts of organic solvent.

The carbohydrate and vinyl compound are mixed in a weight ratio of between 0.3 and 3.0. The catalyst is used in a weight ratio of 3–50% with respect to the carbohydrate. The reaction occurs at ambient temperature and at a strongly acid pH, preferably between 1 and 2. The pH is adjusted by adding a mineral acid.

Alternatively, as the first stage, it is possible to derivatize the enzyme with a vinyl monomer of type

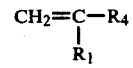

where $R_4$ is H or $CH_3$, and $R_1$ is as heretofore defined, and then copolymerize the derivatized enzyme thus obtained with the carbohydrate.

The reaction between the enzyme and vinyl compound is carried out under pH, time and temperature conditions which favour the bonding reaction between the vinyl compound and enzyme without drastically reducing the enzymatic activity of the latter. Generally, the reaction is carried out at a pH of 5–9, for a period of 30 minutes to 24 hours, and at a temperature of 4°–25° C.

The copolymerization of the derivatized enzyme with the carbohydrate is generally carried out under the same conditions as used for the copolymerization of the vinyl monomer with the carbohydrate.

(2) If the vinyl monomer has not previously been reacted with the enzyme, the copolymer obtained from the reaction between the carbohydrate and vinyl compound is reacted either directly or by way of suitable difunctional compounds with an enzyme.

Because the enzyme reacts mostly through the free amino groups, if in the compound of formula (II) $R_1$ is COOH, this compound can be made to react directly with the enzyme in solution, in the presence of a suitable condensing agent such as a carbodiimide, so that —CO—NH amido bonds form between the macromolecules and enzyme.

If $R_1$ is CHO, the compound (II) can again be made to react directly with the enzyme, with which it forms —CH=NH imino bonds, which can be reduced by suitable reducing agents to —CH$_2$—NH$_2$ bonds.

However, if in compound (II) $R_1$ is —CONH$_2$, it is necessary to react it with a difunctional reagent such as a dialdehyde to give a compound of formula:

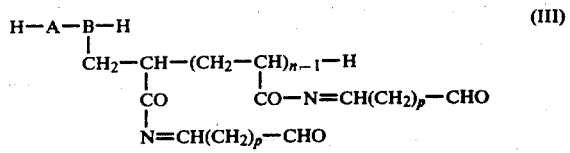

in which n is as heretofore defined, and p is a whole number from 0 to 5. The terminal CHO groups thus introduced react with the amino groups of the enzyme to form —CH=N—E imino bonds. The reaction between compound (II) and the dialdehyde is carried out in an aqueous solvent at a temperature of between 20° and 40° C. for a time of between 2 and 48 hours.

The reaction with the enzyme is carried out, after separating the unreacted products, at a pH of between 6 and 8, at a temperature of between 4° and 25° C. and for a period of between 2 and 24 hours, with the enzyme quantity being related to the quantity of enzyme which it is required to immobilize.

Alternatively, the —CO—NH₂R₁ groups of compound (II) can be converted into azide groups by reaction with hydrazine and then with nitrous acid in accordance with the scheme:

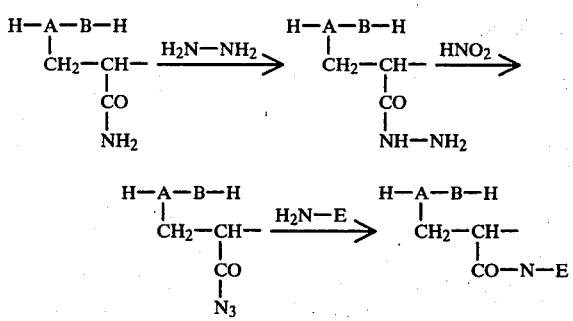

The reaction with 6 M hydrazine is carried out at 50° C. for 6 to 24 hours, then dialyzing the product obtained, dissolving the hydrazine in HCl at 0°–2° C., adding a NaNO₂ solution drop by drop and purifying the reaction product in cooled acetone (2° C.). The azide compound is reacted with the enzyme in aqueous phase at a pH of 7–8, at a temperature of about 4° C. for 2 to 24 hours.

(3) The copolymer obtained by the reaction between the carbohydrate and vinyl compound is modified by introducing free —SH groups into its structure following various alternatives. According to the method chosen for introducing the —SH groups, the sulphydrylation reaction is carried out either before or after the introduction of the enzyme radicals. In this respect, it must be remembered that at a pH exceeding 8–8.5 and at a temperature exceeding 4° C. the enzyme becomes deactivated even over short reaction times.

(A) A convenient method used for sulphydrylating the compounds according to the invention consists of reacting compounds (II) with epichlorohydrin in an alkaline (a) or acid (b) environment, then treating the compound obtained with thiosulphate and finally reducing the thiosulphate groups to —SH groups. Schematically, the reaction sequence can be indicated as follows:

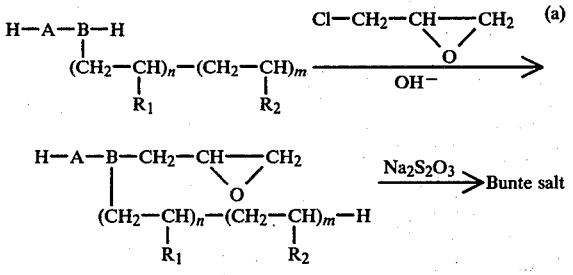

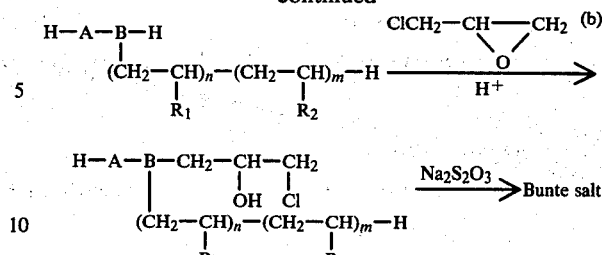

The Bunte salt formed can be reduced either by decomposition with mineral acids or by treatment with reducing agents of NaBH₄, dithioerythritol, mercaptoethanol or other types, to sulphydrylated compounds of formula:

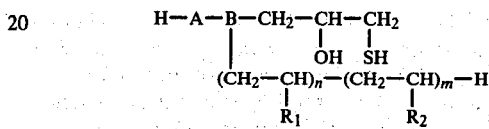

in which R₁ and R₂ are as heretofore defined. It is apparent that —R₃E groups, in which R₃ and E are as heretofore defined, can be present instead of the R₁ groups.

The reaction with epichlorohydrin in a basic environment is carried out at a temperature of between 25° and 80° C. for a time of between 4 and 24 hours. The reaction with epichlorohydrin in an acid environment is carried out at a temperature of between 80° and 100° C. for a time of between 8 and 24 hours. The reaction with Na₂S₂O₃ is carried out in a buffer phosphate solution at pH 6.3 overnight. The reduction reaction is carried out at a pH 6–7 in a buffer.

(B) As an alternative to the preceding method, the sulphydrylation reaction can be carried out by reacting the compounds (II) with epichlorohydrin, then reacting the epoxy derivative obtained with cysteine hydrochloride in an aqueous environment at pH 10–12 or in a mixed solvent consisting of water with a dipolar aprotic solvent (dimethylsulphoxide, dimethylformamide etc.) at a pH 10–12 for 15 hours at ambient temperature. The disulphide groups of the cysteine are then reduced to SH groups with sodium borohydride.

(C) The sulphydrylation of the polysaccharides can also be carried out by direct esterification of the polysaccharide with thioglycolic acid at a temperature of 80° C. in the presence of a mineral acid or Lewis acids. The need to operate in the presence of acid catalysts reduces the applicability of the method to those polysaccharides which do not hydrolyze under the conditions adopted for the esterification reaction.

(D) Another method for introducing sulphydryl groups consisting of preparing the tosyl derivative of the polysaccharide, followed by reaction with potassium sulpho-acetate and subsequent decomposition by alkaline hydrates, according to the reaction scheme:

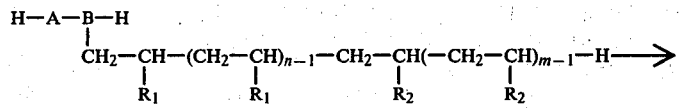

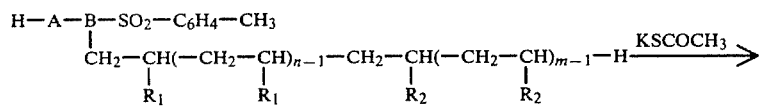

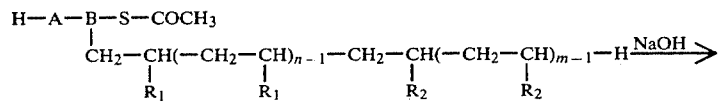

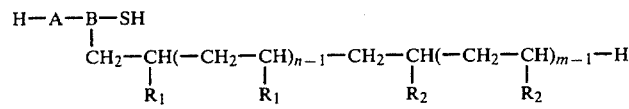

The reaction with tosyl chloride is carried out in pyridine at 70° C., then washing with a mixture of water and pyridine and finally extracting with acetone.

The reaction with KSCOCH$_3$ is carried out in methanol, acetone or dimethylformamide at a temperature of between 50° and 70° C. for a period of up to 48 hours. The decomposition of the xanthogenic radical is carried out with 2% alkaline hydrate for one hour.

The sequence of the derivatization reactions of the —A—B— radical in formula (I) can also be reversed with respect to the said stages 1,2,3.

It is therefore possible, for example, to introduce protected sulphydryl groups on the carbohydrate and then copolymerize the carbohydrate with the vinyl monomers. The enzyme is derivatized on the product.

Alternatively, it is also possible to derivitize the enzyme on a vinyl monomer and react the sulphydrylated carbohydrate with this product.

Some of the preferred alternatives for the process according to the present invention are illustrated in the following examples, which are however non-limiting.

EXAMPLE 1

8 grams of saccharose are dissolved in 16 ml of 0.1 HNO$_3$ and 40 ml of isopropyl alcohol. After deaeration by means of a nitrogen current, a solution of 0.970 grams of cerium ammonium nitrate in 10 ml of HNO$_3$ and a solution of 10 grams of acrylamide in 16 ml of 0.1 HNO$_3$ are added simultaneously. The copolymerization reaction is carried out overnight at ambient temperature under a nitrogen stream.

Any non-reacted MA is eliminated by ultrafiltration, together with the lowest molecular weight portions of the copolymer. The solution is reacted with epichlorohydrin for 1-4 hours at 60° C. in a 0.1-1 M NaOH environment. The solution is extracted with chloroform until the unreacted epichlorohydrin disappears in the concentrated extract.

The solution is buffered with potassium phosphate at pH 6.3, and 1-2 M sodium thiosulphate is added.

The reaction is carried out for 2-24 hours at ambient temperature. The solution is adjusted to pH 6.5-8 and treated with 50% glutaraldehyde at 20°-40° C. for 20-50 hours. It is dialyzed against water until the unreacted glutaraldehyde disappears in the dialysis water, and the solution is then lyophilized. The copolymer obtained is reacted with deoxyribonuclease at 4° C. in a buffer solution at pH of 6 to 8.5 for a time of 2 to 24 hours. The unreacted carbonyl groups are then reduced to hydroxyl groups and the thiosulphonic groups to thiol groups with sodium borohydride in the presence of calcium salts in order not to deactivate the enzyme.

The preparation can be easily dispersed in water and propylene glycol and can be preserved even at ambient temperature for long time periods. The quantity of —SH groups per gram of product varies between 20 and 200 micromoles/g depending on the reaction conditions.

The enzymatic activity lies between 10,000 and 120,000 U/g.

EXAMPLE 2

Following the procedure described in Example 1, saccharose was copolymerized simultaneously with acrylamide and acrylic acid to give products more soluble in the water phase, these products precipitating around pH 4 and being completely soluble at pH values exceeding 7.

The content of SH groups and the enzymatic activity are similar to those given for example 1.

EXAMPLE 3

Following the procedure described in Example 1, a saccharose-polyacrylamide polymer was prepared and treated with 6 M hydrazine at 50° C. for 18-20 hours. Under these conditions, the amido groups are converted into hydrazide groups. The thiosulphonic groups are introduced as described in Example 1.

The mixture is treated with 0.1 N HCl at 0.2° C., and a 13% solution of NaNO$_2$ is then added drop by drop while maintaining the temperature at 0°-20° C. The excess HNO$_2$ is destroyed with sulphamic acid, the mixture is dialyzed in a cold chamber at 2° C., and then precipitated in cold acetone.

The azide copolymer, with an azide group content of between 2 and 20 meq/g, is reacted in a borax buffer at pH 8.5 with different trypsin preparation at a temperature of 4° C. for 2-6 hours. The thiosulphonic groups are then reduced with sodium borohydride as described in Example 1. The compound can be dispersed in water and propylene glycol.

The enzymatic activity of the preparation is between 5 and 15% of that introduced into the reaction.

EXAMPLE 4

The saccharose is suspended in epichlorohydrin and refluxed under stirring for 2-5 hours in the presence of 37% HCl or HClO$_4$ as catalysts. The product is precipitated in acetone and dried.

The material is suspended in an aqueous thiosulphate solution, the pH adjusted to neutrality, and the reaction carried out for 1-12 hours under reflux over a water bath.

After cooling, the solution is concentrated and precipitated in ethanol. The treatment with thiosulphate can be repeated until complete substitution of the Cl groups is introduced.

The product is copolymerized with acrolein and acrylic acid or vinylpyrrolidone, using cerium salts as the initiation system.

The copolymer is reacted with deoxyribonuclease initially in a buffer at a pH of between 6.5 and 8.5 at 4° C. for 4-24 hours.

The sample is then treated with sodium borohydride and lyophilized. The content of —SH groups lies between 5 and 100 micromoles/g of copolymer, the enzymatic activity lying between 50,000 and 250,000 U/g.

EXAMPLE 5

10 g of saccharose in 100 ml of N NaOH are reacted with 10 ml of epichlorohydrin for 4 hours at 60° C.

The unreacted epichlorohydrin is extracted with chloroform, and the reaction product is reacted with excess cysteine hydrochloride in an aqueous solvent or in a mixed solvent (water-dimethylsulphoxide) at pH 11 for 4-15 hours at ambient temperature. After separation, the reaction product is copolymerized with acrolein or a mixture of acrolein and vinylpyrrolidone as in Example 4. After reaction with deoxyribonuclease I, the sample is reduced with sodium borohydride and then lyophilized.

The content of —SH groups lies between 100 and 400 micromoles/g, the enzymatic activity lying between 250,000 and 500,000 U/g of copolymer.

EXAMPLE 6

As described in Example 4, the saccharose is treated under acid conditions with epichlorohydrin and then with thiosulphate.

The deoxyribonuclease is reacted separately with acrolein in a buffer at pH of between 6.5 and 8.5, for a time of between 2 and 24 hours, correcting the reaction pH with NaOH during the first two hours.

The enzyme derivatized on the saccharose is copolymerized in the presence of acrylic acid using $Fe^{++}/H_2O_2$ as the redox system.

Dialysis against water is then carried out until the disappearance of any unreacted acrolein or acrylic acid in the dialysis water, the product then being reduced with sodium borohydride and lyophilized.

The content of SH groups and the enzymatic activity are similar to those determined for the product of Example 4.

EXAMPLE 7

A solution of saccharose in 3:1 pyridine:$H_2O$ is distilled until the complete removal of the water as azeotrope (93°-94° C.). When the temperature reaches 113°-114° C., distillation is interrupted and the mixture cooled. Tosyl chloride is added and the reaction is allowed to proceed overnight at ambient temperature.

The reaction mixture is precipitated in an ethanol:-$H_2O$ mixture, filtered and a 2.5% solution of potassium sulphoacetate in dimethyl formamide is added. The reaction is carried out for 75 hours at 70° C. After cooling, the product is precipitated in ethyl alcohol and dried.

The product is treated with 2% NaOH at ambient temperature for 1 hour, then neutralized with 1 N HCl and precipitated with ethanol.

In a like manner to example 6, the deoxyribonuclease is derivatized with glycidyl methacrylate at a pH of between 6 and 8 in a buffer, for a time of 2 to 24 hours. The derivatized enzyme is copolymerized with the saccharose in the presence of acrylic acid using a $Fe^{++}/H_2O_2$ redox system.

The reaction mixture is dialyzed against water until the disappearance of any unreacted glycidyl methacrylate. Reduction with sodium borohydride is then carried out.

The compound is dispersible with difficulty in the aqueous phase. The content of —SH groups lies between 50 and 150 micromoles/g, and the enzymatic activity lies between 10,000 and 30,000 U/g.

The compounds prepared according to the present invention have been tested with regard to their mucolytic activity both "in vitro" and "in vivo". Having ascertained in a preliminary screening that all the compounds prepared according to the preceding examples possess mucolytic activity, a thorough study was made with two of these compounds, namely the product of Example 1, or ET 1014, and the product of Example 5, or ET 1015, in comparison with N-acetyl-cysteine and deoxyribonuclease.

The mucolytic activity was determined both on mucopurulent expectoration and on purulent expectoration of patients suffering from chronic bronchitis and/or bronchiectasia. The method used was that described by Lieberman (Amer.Rev. Resp.Dis. 97, 662, 1968) which uses a Brockfield cone-plate microviscovimeter, at different speeds (from 0.5 to 100 rpm), temperature-controlled at 37° C., with a circulation bath provided with a Foxboro pneumatic recorder and a compressor delivering compressed air at 15 atmospheres.

Mucolytic activity was measured after 5, 10 and 20 minutes from the beginning of the test, and was expressed as a percentage reduction in the initial viscosity. Each value is the mean of 20 determinations made twice on the expectoration of 10 patients, and is expressed as a percentage of the total base values, at the different rotational speeds used.

All the tested products were solubilized and/or solu-suspended in the same volume of physiological solution.

Table 1 shows the results obtained on mucopurulent expectoration, and Table 2 shows the results obtained on purulent expectoration.

From the values given in the tables, it is apparent that the compounds Et 1014 ET 1015 are constantly and considerably more active either than N-acetylcysteine or deoxyribonuclease when used separately.

With regard to the results obtained with deoxyribonuclease+N-acetylcysteine, the low activity of the mixture is probably due to the deactivating of the enzyme by the N-acetylcysteine.

The compounds according to the invention practically attain their maximum activity after 5 minutes and at a concentration of 5%.

TABLE 1

| % reduction in initial viscosity at various times in minutes | | | |
|---|---|---|---|
| Product | 5 min. | 10 min. | 20 min. |
| N.acetylcysteine | | | |
| conc. 20% | 60.4 ± 13.2 | 62.1 ± 10.8 | 60.5 ± 7.2 |
| conc. 10% | 54.9 ± 9.5 | 59.7 ± 7.5 | 57.2 ± 5.9 |
| conc. 5% | 42.6 ± 11.7 | 48.3 ± 5.4 | 51.6 ± 7.6 |
| Et 1014 | | | |
| conc. 20% | 86.8 ± 8.3 | 85.9 ± 8.2 | 87.5 ± 7.7 |
| conc. 10% | 82.5 ± 7.9 | 83.1 ± 8.4 | 82.3 ± 8.3 |
| conc. 5% | 79.7 ± 8.5 | 80.4 ± 7.9 | 81.2 ± 6.8 |

TABLE 1-continued

| % reduction in initial viscosity at various times in minutes | | | |
|---|---|---|---|
| Product | 5 min. | 10 min. | 20 min. |
| Et 1015 | | | |
| conc. 20% | 93.8 ± 6.8 | 92.2 ± 7.1 | 93.1 ± 7.0 |
| conc. 10% | 94.2 ± 7.2 | 93.8 ± 6.6 | 99.4 ± 6.3 |
| conc. 5% | 90.5 ± 6.3 | 91.6 ± 6.5 | 90.8 ± 6.9 |
| Deoxyribonuclease | | | |
| 150,000 units | 39.2 ± 2.9 | 40.5 ± 3.6 | 43.4 ± 3.4 |
| 75,000 units | 37.4 ± 3.5 | 41.2 ± 3.1 | 41.6 ± 2.8 |
| 25,000 units | 35.6 ± 4.1 | 39.8 ± 2.7 | 40.9 ± 3.7 |
| Deoxyribonuclease | | | |
| 150,000 units + N.acetylcysteine conc. 5% | 40.2 ± 4.5 | 49.6 ± 3.8 | 47.2 ± 3.6 |

TABLE 2

| % reduction in initial viscosity at various times in minutes | | | |
|---|---|---|---|
| Product | 5 min. | 10 min. | 20 min. |
| N.acetylcysteine | | | |
| conc. 20% | 51.6 ± 7.2 | 52.9 ± 6.9 | 53.2 ± 6.1 |
| conc. 10% | 43.5 ± 6.8 | 42.3 ± 6.4 | 44.6 ± 6.6 |
| conc. 5% | 37.2 ± 6.1 | 40.5 ± 5.3 | 41.9 ± 4.8 |
| Et 1014 | | | |
| conc. 20% | 92.1 ± 6.9 | 90.8 ± 7.3 | 91.6 ± 5.9 |
| conc. 10% | 89.4 ± 5.2 | 87.3 ± 6.2 | 86.5 ± 8.2 |
| conc. 5% | 87.5 ± 6.4 | 85.4 ± 7.0 | 84.3 ± 5.8 |
| Et 1015 | | | |
| conc. 20% | 94.3 ± 5.6 | 92.5 ± 8.4 | 93.2 ± 9.1 |
| conc. 10% | 86.2 ± 6.8 | 89.7 ± 7.1 | 89.1 ± 7.2 |
| conc. 5% | 87.4 ± 7.2 | 88.4 ± 6.6 | 90.5 ± 6.9 |
| Deoxyribonuclease | | | |
| 150,000 units | 82.6 ± 6.8 | 80.4 ± 6.6 | 79.4 ± 6.4 |
| 75,000 units | 80.4 ± 7.5 | 77.1 ± 7.1 | 78.7 ± 5.9 |
| 25,000 units | 77.9 ± 5.4 | 74.6 ± 7.2 | 73.9 ± 7.3 |
| Deoxyribonuclease | | | |
| 150,000 units + N.acetylcysteine conc. 5% | 36.5 ± 5.9 | 37.2 ± 4.6 | 35.9 ± 4.2 |

The DL 50 of the products Et 1014 and Et 1015 was evaluated on rats of Sprague-Dawley stock and mice of Swiss stock by oral administration. In both species of rodents, the DL 50 was greater than 3 g/kg.

The products Et 1014 and Et 1015 were also administered to 10+10 patients affected by otorhinolaryngologic illnesses characterised by purulent and/or mucopurulent secretion, and to 10+10 patients affected by bronchiecstasic chronic bronchitis with a high level of purulent and/or mucopurulent expectoration.

The dose was two aerosol applications per day, each comprising 1 g of product dissolved in distilled water, for an average time of 10 days.

The secretions of the respiratory tracts demonstrated a considerable reduction in viscosity with a clear improvement in the expectoration in the case of bronchial illnesses, and an almost total disappearance of the symptomatology of otorhinolaryngologic affections.

The tolerance was excellent in all patients both with Et 1014 and with Et 1015, and in particular no local or general manifestations of intolerance appeared which could be imputed to the two products.

In conclusion, the new products have proved practically free from toxicity, give no side or intolerance effects of any kind, in that they are not absorbed by the tissues, and have a very high mucolytic activity both on purulent and mucopurulent secretions.

No mucolytic drug known at the present time possesses this collection of properties.

The new products can, for example, be used either topically or by aerosol in the following affections:
- bronchial affections or affections of the otorhinolaryngologic system with mucous secretion
- in the treatment of torpid ulcers or where viscous secretion of high protein content exists
- for bladder washing in chronic infections
- in the treatment of acne by cleaning cell debris
- for eliminating protein and mucopolysaccharide residues in contact lenses.

What we claim is:

1. A compound having mucolytic activity while not being absorbed by tissues of the formula

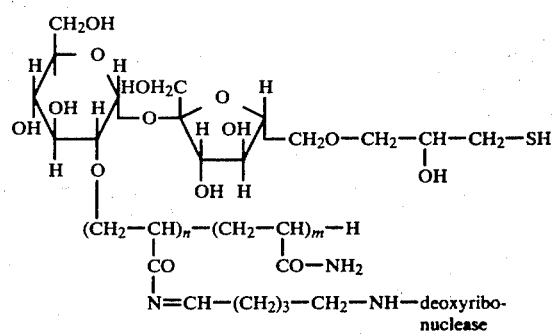

wherein n+m is 500.

2. A compound having mucolytic activity while not being absorbed by tissues of the formula

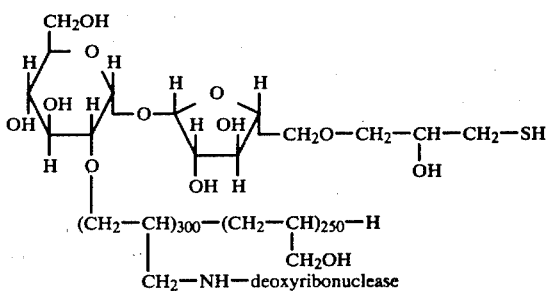

* * * * *